US009985255B2

(12) United States Patent
Nielsen et al.

(10) Patent No.: US 9,985,255 B2
(45) Date of Patent: May 29, 2018

(54) BATTERY ENCASEMENT FOR IMPLANTABLE DEVICES

(71) Applicant: Medtronic, Inc., Minneapolis, MN (US)

(72) Inventors: Christian S. Nielsen, River Falls, WI (US); John K. Day, Chandler, AZ (US); Erik J. Hovland, Minnetonka, MN (US); Jody J. Klaassen, Minneapolis, MN (US); Prabhakar A. Tamirisa, Brooklyn Park, MN (US); Collette M. Vanelzen, Zimmerman, MN (US)

(73) Assignee: Medtronic, Inc., Minneapolis, MN (US)

( * ) Notice: Subject to any disclaimer, the term of this patent is extended or adjusted under 35 U.S.C. 154(b) by 534 days.

(21) Appl. No.: 14/639,297

(22) Filed: Mar. 5, 2015

(65) Prior Publication Data

US 2016/0260938 A1 Sep. 8, 2016

(51) Int. Cl.
*H01M 2/02* (2006.01)
*H01M 2/08* (2006.01)
(Continued)

(52) U.S. Cl.
CPC .......... *H01M 2/0202* (2013.01); *A61N 1/378* (2013.01); *H01M 2/027* (2013.01);
(Continued)

(58) Field of Classification Search
None
See application file for complete search history.

(56) References Cited

U.S. PATENT DOCUMENTS 7,662,509 B2   2/2010   Howard et al.
7,682,745 B2   3/2010   Howard et al.
(Continued)

FOREIGN PATENT DOCUMENTS

| EP | 0061966 | 10/1982 |
| EP | 0800843 | 10/1997 |
| EP | 0801958 | 10/1997 |
| FR | 2466256 | 4/1981 |

OTHER PUBLICATIONS (PCT/US2016/019716) PCT Notification of Transmittal of the International Search Report and the Written Opinion of the International Searching Authority, dated May 2, 2016, 7 pages.

*Primary Examiner* — Daniel Gatewood
(74) *Attorney, Agent, or Firm* — Sorell Lenna & Schmidt, LLP

(57) ABSTRACT

Various embodiments of a battery assembly include a first housing shell, a second housing shell, an insulator and battery components. The first housing shell has a first perimeter side wall, a first housing bottom, and a first contact area on the first housing bottom. The second housing shell has a second perimeter side wall, a second housing bottom, and a second contact area on the second housing bottom. The second housing shell is disposed in the first housing shell with the second contact area opposing the first contact area. The insulator is interposed between the first housing shell and the second housing shell to effect electrical insulation between the first housing shell and the second housing shell. The battery components include an anode electrode, a cathode electrode, and a separator interposed between the cathode electrode and the anode electrode. The separator contains an electrolyte.

18 Claims, 7 Drawing Sheets

(51) Int. Cl.
   *H01M 10/42* (2006.01)
   *A61N 1/375* (2006.01)
   *H01M 2/16* (2006.01)
   *H01M 10/04* (2006.01)
   *A61N 1/378* (2006.01)
   *H01M 10/052* (2010.01)

(52) U.S. Cl.
   CPC ....... *H01M 2/0217* (2013.01); *H01M 2/0277* (2013.01); *H01M 2/08* (2013.01); *H01M 2/166* (2013.01); *H01M 10/0436* (2013.01); *H01M 10/425* (2013.01); *H01M 10/4257* (2013.01); *H01M 10/052* (2013.01); *H01M 2220/30* (2013.01)

(56) References Cited

U.S. PATENT DOCUMENTS

| | | |
|---|---|---|
| 7,740,985 B2 | 6/2010 | Howard et al. |
| 7,794,869 B2 | 9/2010 | Howard et al. |
| 7,803,481 B2 | 9/2010 | Howard et al. |
| 7,807,299 B2 | 10/2010 | Howard et al. |
| 7,811,705 B2 | 10/2010 | Scott et al. |
| 7,931,987 B2 | 4/2011 | Howard et al. |
| 8,065,006 B2 | 11/2011 | Rorvick et al. |
| 2009/0162743 A1* | 6/2009 | Nam ............... H01M 2/023 429/110 |
| 2013/0295435 A1* | 11/2013 | Vu ............... H01M 2/0217 429/157 |

* cited by examiner

BATTERY ENCASEMENT FOR IMPLANTABLE DEVICES

TECHNICAL FIELD

The present invention relates to electrochemical power cells and assemblies incorporating such power cells. In particular, various embodiments of the present disclosure are suitable for a variety of applications including applications involving electronic assemblies which are used in medical devices that may optionally be implanted in or carried on a patient.

BACKGROUND

Electrochemical cells in the form of batteries are widely used to power electronic devices. With advances in miniaturizing and/or integrating electronic components devices with ever increasing functionality are being developed. In certain applications, small size and reliable power supplying capability are highly desirable. One such application is in medical devices such as sensors, for example, glucose or oxygen sensors, activity monitors, stimulators such as neuro stimulators or pace makers, or other devices which rely on electrical power to function. Medical devices that are implantable require high reliability, small size, and long term power supplies. Furthermore, such power supplies may be reliably sealed to prevent leakage of electrochemical cell material. Still further, as applications for such devices increase, a greater need exists for power supplies that can be economically produced.

Many types of batteries exist. However, a typical problem with common place batteries is the possibility of leakage of electrolyte chemicals from the batteries with age or abnormal loading of the batteries. Highly reliable sealed electronic packages include hermetically welded assemblies which utilize glass to metal sealed feedthroughs. However, such packaging is expensive to produce due to assembly costs.

Typically, an electronic assembly is connected to a battery and both items are then assembled in a further package. Combining multiple devices, each in their own packaging into a further package make reducing size of such assemblies difficult because the assembly involves putting packages inside other packages.

New electrochemical power supplies are needed which provide reliably sealed, small size, and low cost packaging. Additionally, such power supplies should facilitate housing electronics to keep the overall size of a device small.

SUMMARY

Various embodiments of a battery assembly are provided which effect reliable sealing of battery components while maintaining a small size and low production cost. Still further, embodiments of battery housings are presented that allow incorporation of electronic assemblies into the battery housing. However, the present disclosure does not require that any of the aforesaid attributes be effectuated by embodiments disclosed herein and described in the appended claims.

Briefly stated, embodiments of a battery assembly include a first housing shell, a second housing shell, an insulator and battery components. The first housing shell has a first perimeter side wall, a first housing bottom, and a first contact area on the first housing bottom. The second housing shell has a second perimeter side wall, a second housing bottom, and a second contact area on the second housing bottom. The second housing shell is disposed in the first housing shell with the second contact area opposing the first contact area. The insulator is interposed between the first housing shell and the second housing shell to effect electrical insulation between the first housing shell and the second housing shell. The battery components include an anode electrode, a cathode electrode, and a separator interposed between the cathode electrode and the anode electrode. The separator contains an electrolyte.

The present disclosure provides an embodiment of a battery assembly that comprises a first housing shell having a first perimeter side wall, a first housing bottom, and a first contact area on the first housing bottom, a second housing shell having a second perimeter side wall, a second housing bottom, and a second contact area on the second housing bottom, and the second perimeter side wall having a second housing top edge. The second housing shell is nested in the first housing shell with the second contact area opposing the first contact area. An insulator is interposed between the first housing shell and the second housing shell to effect electrical insulation between the first housing shell and the second housing shell. In some embodiments, a medical device includes a battery assembly, as described herein, and the medical device may be implanted in or carried on a patient.

Battery components comprise an anode electrode electrically contacting one of the first contact area or the second contact area, a cathode electrode electrically contacting another one of the first contact area or the second contact area, and a separator interposed between the cathode electrode and the anode electrode, the separator including an electrolyte. The first housing bottom of the first housing shell opposes the second housing bottom of the second housing shell to define a battery component cavity in conjunction with the first perimeter side wall of the first housing shell, and the anode electrode, the separator, and the cathode electrode are disposed in the battery component cavity. At least one of the first perimeter side wall or the second perimeter side wall in conjunction with the second housing bottom defines an electronic assembly cavity. The first housing shell includes at least one first contact projecting from the first perimeter side wall. The second housing shell includes at least one second contact projecting from the second perimeter side wall. The insulator is a molded insulator configured to form a sleeve between the first and second housing shells and an edge flange overlapping the second housing top edge. An electronic assembly is disposed on the edge flange and has electronic components disposed, at least in part, in the electronic assembly cavity. The at least one first contact and the at least one second contact are deformed to effect electrical contact with the electronic assembly to provide power from the battery components and to retain the electronic assembly within the electronic assembly cavity.

In another embodiment of the present disclosure, there is provided a battery assembly that comprises a first housing shell having a first perimeter side wall, a first housing bottom, and a first contact area on the first housing bottom. The first perimeter side wall extends from the first housing bottom to a first housing perimeter edge. A second housing shell has a second perimeter side wall, a second housing bottom, and a second contact area on the second housing bottom. The second perimeter side wall extends from the second housing bottom to a second housing perimeter edge above the second housing bottom, and the second perimeter side wall has a U-fold section extending from the second housing bottom to a second side wall bottom edge. The second housing shell is nested in the first housing shell with the second contact area opposing the first contact area. An insulator is interposed between the first housing shell and the second housing shell to effect electrical insulation between the first housing shell and the second housing shell. The insulator is disposed on the second housing shell to cover a first side of the U-fold section, the second side wall bottom edge, at least a portion of a second side of the U-fold section, and at least a portion of a section of the second housing perimeter wall extending from the second housing bottom to the second housing perimeter edge. Battery components comprise an anode electrode electrically contacting one of the first contact area or the second contact area, a cathode electrode electrically contacting another one of the first contact area or the second contact area, and a separator interposed between the cathode electrode and the anode electrode, with the separator including an electrolyte. The first housing bottom of the first housing shell opposes the second housing bottom of the second housing shell to define a battery component cavity in conjunction with the U-fold section of the second perimeter side wall of the second housing shell. The anode electrode, the separator, and the cathode electrode are disposed in the battery component cavity. The first perimeter side wall and the second perimeter side wall, in conjunction with the second housing bottom, define an electronic assembly cavity. The first perimeter side wall has a first side wall section including at least one first contact projecting therefrom. The first housing perimeter edge is disposed further from the second housing bottom than the second housing perimeter edge at the first side wall section. The insulator is disposed on the first perimeter side wall extending from a position interposed between the first perimeter side wall and the second perimeter side wall at the first side wall section to at least a position between the second housing perimeter edge and the first housing perimeter edge. The second perimeter side wall has a second side wall section including at least one second contact projecting therefrom. The second housing perimeter edge is disposed further from the second housing bottom than the first housing perimeter edge at the second side wall section. The insulator is disposed on the second perimeter side wall extending from a position interposed between the first perimeter side wall and the second perimeter side wall at the second side wall section to at least a position between the first housing perimeter edge and the second housing perimeter edge. An electronic assembly is connected to the at least one first contact and the at least one second contact and has electronic components disposed, at least in part, in the electronic assembly cavity.

The above, and other objects, features and advantages of the present disclosure will become apparent from the following description read in conjunction with the accompanying drawings. The present disclosure is considered to include all functional combinations of the above described features and corresponding descriptions contained herein, and all combinations of further features described herein, and is not limited to the particular structural embodiments shown in the figures as examples. The scope and spirit of the present disclosure is considered to include modifications as may be made by those skilled in the art having the benefit of the present disclosure which substitute, for elements presented in the claims, devices or structures upon which the claim language reads or which are equivalent thereto, and which produce substantially the same results associated with those corresponding examples identified in this disclosure for purposes of the operation of this invention. Additionally, the scope and spirit of the present disclosure is intended to be defined by the scope of the claim language itself and equivalents thereto without incorporation of structural or functional limitations discussed in the specification which are not referred to in the claim language itself.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1b is a front, top and right side perspective view of the first embodiment of a battery housing of FIG. 1a;

FIG. 6b is a cross-sectional view of the battery housing of FIG. 6a;

Figure 1A:
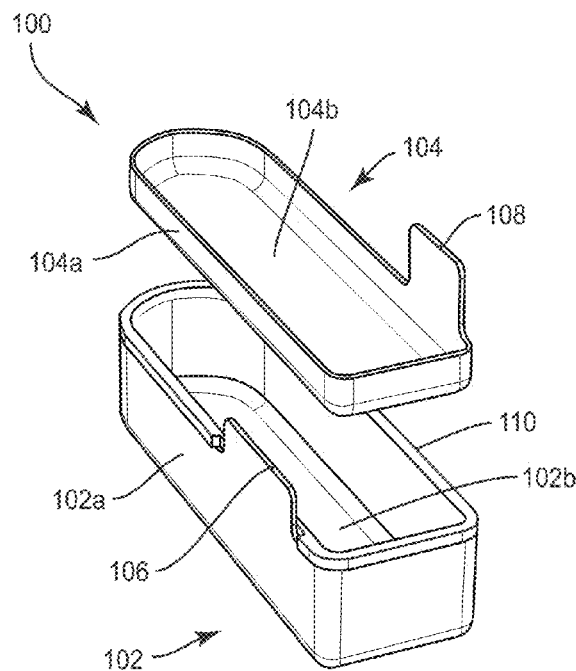
FIG. 1a is a front, top and right side perspective partially exploded view of a first embodiment of a battery housing of the present disclosure.

It is to be understood that the figures are not drawn to scale unless so noted. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

As used in this specification and the appended claims, in some embodiments, the singular forms "a," "an," and "the," include plural referents unless expressly and unequivocally limited to one referent. Thus, for example, reference to "an anode" includes one, two, three or more anodes. It is additionally noted that, as used in the specification and appended claims, relative terminology concerning orientation such as "top," "bottom," "over," and "under" is intended only to describe embodiments disclosed herein in relation to the figures of the present disclosure and do not require any particular orientation in actual application of the described embodiments. In this respect, use of such terms in the claims is intended only to describe relative interrelationship of claim elements to each other and not to describe elements in relation to real world coordinates and directions. Thus, describing an element "A" as a "top" and element "B" as a "bottom" does not preclude reading the claim on a device having an actual orientation wherein "A" is below "B" if inverting the device will place "A" above "B".

Reference is made in detail to various embodiments of the present disclosure, examples of which are illustrated in the accompanying drawings. While the embodiments of the present disclosure are described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims. Furthermore, the present disclosure includes addition of each feature of particular disclosed embodiments to each of the other disclosed embodiments which are absent such feature. Still further, the present disclosure includes substitution of each feature of particular disclosed embodiments for corresponding features of each of the other disclosed embodiments.

In an optional variation of prior described embodiments, the first housing bottom of the first housing shell opposes the second housing bottom of the second housing shell to define a battery component cavity in conjunction with the first perimeter side wall of the first housing shell, and the anode electrode, the separator, and the cathode electrode are disposed in the battery component cavity.

A further optional variation of any of the above embodiments includes an embodiment wherein at least one of the first perimeter side wall or the second perimeter side wall in conjunction with the second housing bottom define an electronic assembly cavity.

An optional feature of any of the above embodiments includes the first housing shell having at least one first contact projecting from the first perimeter side wall. A still further optional feature includes the second housing shell having at least one second contact projecting from the second perimeter side wall.

Another optional feature of any of the above embodiments comprises an electronic assembly disposed in the electronic assembly cavity, and the at least one first contact and the at least one second contact electrically contacting the electronic assembly to provide power from the battery components.

Yet another optional feature of any of the above embodiments comprises the insulator being an insulating film laminated on at least one of the first housing shell and the second housing shell.

Still another optional feature of any of the above embodiments comprises the insulator including at least one of fibers, alumina particles, or glass spheres configured to effect separation and electrical isolation of the first housing shell and the second housing shell. In a particular variation, the fibers are Kevlar fibers.

A further optional feature of any of the above embodiments comprises the insulator being a molded insulator configured to form a sleeve between the first and second housing shells. Optionally provided is a flange around a top edge of the insulator.

A still further optional feature of any of the above embodiments comprises the second perimeter side wall including a U-fold extending from a junction with the second housing bottom toward the first housing bottom and defining at least a portion of the battery components cavity. Yet another optional feature comprises the U-fold having first and second opposite outer surfaces and the insulator being disposed on the first and second opposite outer surfaces.

Another further optional feature of any of the above embodiments comprises the second perimeter side wall having a perimeter edge defining an opening aperture of the second housing shell and a perimeter flange extending outward from the perimeter edge in a direction away from an interior of the second housing shell. In some embodiments, this feature includes the second housing being disposed within the first housing shell such that the insulator is situated between the perimeter flange and the first housing bottom, and the first housing shell has a cup configuration inverted from a cup configuration orientation of the second housing shell. In some embodiments, this feature includes the first perimeter side wall, the second perimeter side wall, and the perimeter flange defining, at least in part, an inter-shell cavity between the first housing shell and the second housing shell. A sealing compound can be disposed in the inter-shell cavity.

Still another optional feature of any of the above embodiments comprises an electronic assembly disposed in the electronic assembly cavity, and the electronic assembly being electrically connected to the first and second housing shells to provide power from the battery components, wherein the insulator is an insulating film laminated on at least one of the first housing shell and the second housing shell.

Yet another optional feature of any of the above embodiments comprises an electronic assembly disposed in the electronic assembly cavity, and the electronic assembly being electrically connected to the first and second housing shells to provide power from the battery components, wherein the insulator includes at least one of fibers, alumina particles, or glass spheres configured to effect separation and electrical isolation of the first housing shell and the second housing shell.

A still further optional feature of any of the above embodiments includes the separator having portions secured between the insulator and one of the first housing shell and the second housing shell.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Figure 1B:
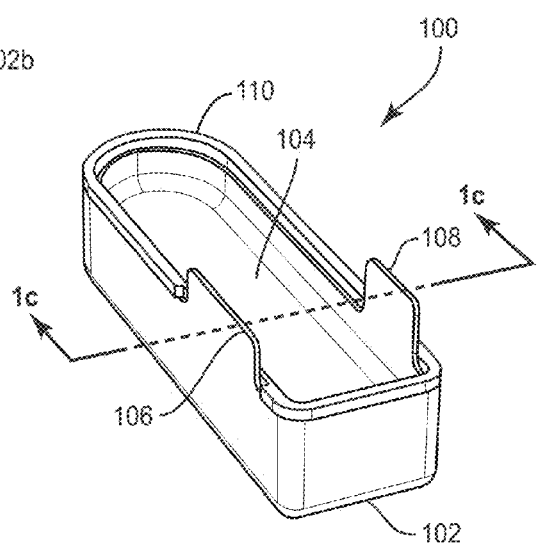
Figure 1C:
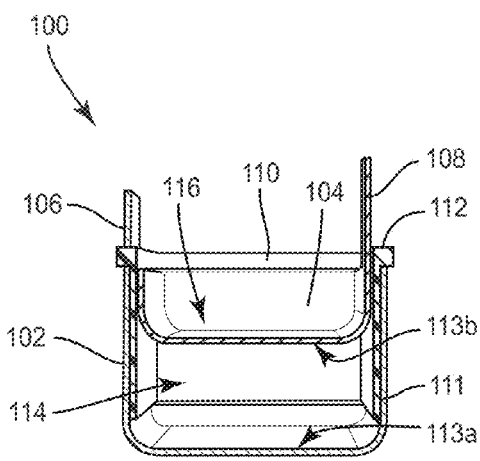
FIG. 1c is a cross-sectional view of the first embodiment of a battery housing taken along line Ic-Ic of FIG. 1b.

Referring to FIGS. 1a-1c, an embodiment of a battery housing 100 has a first housing shell 102 and a second housing shell 104 with an insulating sealing member 110 interposed therebetween. The first and second housing shells, 102 and 104, respectively have first and second electrical contact tabs, 106 and 108, which extend from the first and second housing shells, 102 and 104, and serve to effect electrical connection to an electronic assembly 120. Together, the first and second housing shells, 102 and 104, in conjunction with the insulating sealing member 110, define a battery components cavity 114 and an electronic assembly cavity 116. The first and second housing shells, 102 and 104, are formed into cup configurations respectively having a first and second perimeter side wall, 102a and 104a, defining at top edges (based on orientations depicted) housing apertures, and first and second housing bottoms 102b and 104b. In some embodiments, a medical device includes battery housing 100, as described herein, and the medical device may be surgically implanted in or carried on a patient.

In a first embodiment, the first and second housing shells, 102 and 104, are optionally respectively formed of a titanium foil material of 75 μm and 50 μm thickness which is drawn to form the geometries of the first and second housing shells 102 and 104. Titanium foil is advantageous due to its strength and lightweight, however, it will be appreciated by those skilled in the art that other materials may be used in place of titanium, such as, for example, and not limitation, aluminum, stainless steel, copper, magnesium, or alloys thereof. The thickness of the first and second housing shells, 102 and 104, may be varied to meet mechanical requirements of a given application. Additionally, the first and second housing shells, 102 and 104, need not be formed of like materials as applications may dictate differing material requirements based on environmental conditions of the respective parts. The first and second housing shells, 102 and 104, make contact with battery components to serve as, irrespectively, positive and negative electrodes of the battery components to be installed in the battery components cavity 114.

The insulating sealing member 110 may be formed of any type of insulating material and optionally can be formed of either a film or molded member. In FIGS. 1a-1c, the embodiment of the insulating sealing member 110 is formed of molded polypropylene (PP) material to have a tubular body 111 with a radially protruding flange 112 which sits atop an upper edge of the first housing shell 102. As an example, the PP material is optionally in the form of PPaF, supplied by Dai Nippon Printing, Kyoto, Japan, which contains a fiber such as Kevlar®, or other insulating materials for instance, alumina particles, or glass spheres, thereby providing a significant separation of the first and second housing shells 102 and 104 in any of the embodiments disclosed herein. This configuration ensures a separation such that a minimum seal material thickness is maintained while concurrently maintaining sufficient electrical insulation strength. The insulating sealing member 110 (PPaF, etc.) is not limited to a molded part, and is optionally in the form of a sheet, tape, or extruded tube, or other configuration.

In an embodiment of a sealing configuration, the first housing shell 102 and the second housing shell 104 are bonded together by the delivery of energy to the insulating sealing member 110 to effect reflow of thermoplastic material of the insulating sealing member 110 such that the thermoplastic material wets the first and second housing shells, 102 and 104, thus creating a bond between the two. The energy may be delivered by any method allowing sufficient heat to be applied to effect reflow, such as, for example, and not limitation, hot tooling, inductive heating, or direct or indirect laser heating. Other sealing methods may be employed such as curable materials in the form of epoxies, polymer sealants, or other materials, which may bond to the first and second housing shells 102 and 104.

Figure 1D:
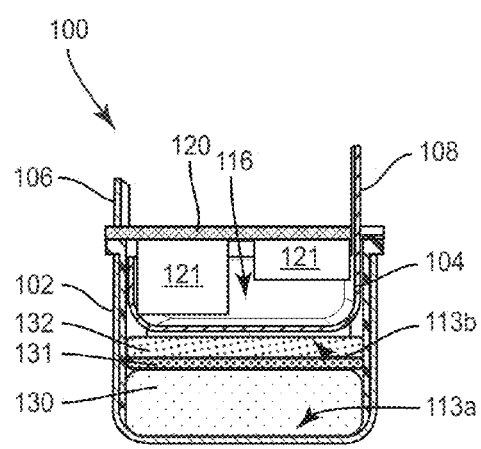
FIG. 1d is a cross-sectional view of the first embodiment of a battery housing of FIG. 1b.

The first housing shell 102 has a first contact area 113a exposed to an interior of the battery components cavity 114 and the second housing shell 104 has a second contact area 113b exposed to permit contact with either of anode and cathode electrodes of the battery components, thus permitting the first and second housing shells, 102 and 104 to conduct power via the first and second electrical contact tabs, 106 and 108, to the electronic assembly 120 connected thereto and situated in the electronic assembly cavity 116, as shown in FIG. 1d.

Referring to FIG. 1d, the battery housing 100 is shown including battery components installed in the battery components cavity 114 and the electronic assembly 120, including electronic components 121, disposed in the electronic assembly cavity 116. In order to make electrical contact with the electronic assembly 120, electrical contact tabs, 106 and 108, are folded over (indicated by arced arrows) onto the electronic assembly 120 to contact bonding pads (not shown). The electronic assembly 120 optionally includes circuitry controlling the battery components to prevent overheating and effect controlled charging. In an embodiment, the electronic assembly 120 is optionally an implantable medical device such as, monitoring sensors including, but not limited to, blood pressure, glucose, activity, cardiac, or other devices both known and yet to be developed. The electronic assembly 120 may also be embodied as circuitry for stimulation including all electro-physiological stimulation, both cardiac rhythm and neurological.

For exemplary purposes and not limitation, lithium ion battery components are discussed herein. However, the present disclosure is not limited to the lithium ion type of battery and any other type of known or yet to be developed battery components may be installed in the battery components cavity 114 and corresponding electronic components cavities of further embodiments discussed herein. Alternative examples include, but are not limited to, primary batteries types such as Zinc-carbon, Zinc-chloride, Alkaline, Nickel oxyhydroxide, Lithium (lithium-copper oxide) Li—CuO, Lithium (lithium-iron disulfide) LiFeS2, Lithium (lithium-manganese dioxide) LiMnO2, Lithium (lithium-carbon fluoride) Li—(CF)n, Lithium (lithium-chromium oxide) Li—CrO2, Mercury oxide, Zinc-air, Zamboni pile, Silver-oxide (silver-zinc), or Magnesium. Additional examples include, but are not limited to, secondary batteries types such as NiCd, Lead-acid, NiMH, NiZn, or AgZn.

Prior to assembly of the first and second housing shells, 102 and 104, the insulating sealing member 110 is inserted into the first housing shell 102. Then, the battery components are installed as shown in FIG. 1*d*. A cathode electrode 130 is installed in the bottom of the battery components cavity 114 to make electrical contact with the first contact area 113*a* of the first housing shell 102. A separator 131 is next installed followed by an anode electrode 132. The separator 131 is optionally embodied as a polymer electrolyte membrane (PEM) which maintains separation of the cathode electrode 130 and the anode electrode 132. Alternative, other electrolyte and separator configurations may be employed. The anode electrode 132 makes electrical contact with the second contact area 113*b* of the second housing shell 104. In an embodiment of the present disclosure, the anode electrode 132 is formed of lithium or composite thereof and the cathode 130 is formed of a material suitable for operation in conjunction with lithium such as, for example and not limitation, iron disulfide, manganese dioxide, carbon fluoride, or chromium oxide. It is to be understood that the arrangement depicted in FIG. 1*d* is exemplary and that the polarity of the battery components with relation to the first and second housing shells, 102 and 104, may be reversed by placing the anode 132 at the bottom in contact with the first contact area 113*a* of the first housing shell 102 and the cathode 103 in contact with the second contact area 113*b* of the second housing shell 104. Still further, the battery components may be preassembled together, or partially preassembled together, and then installed in the battery components cavity 114 in an order required to provide the desired final polarity of the battery.

Figure 1E:
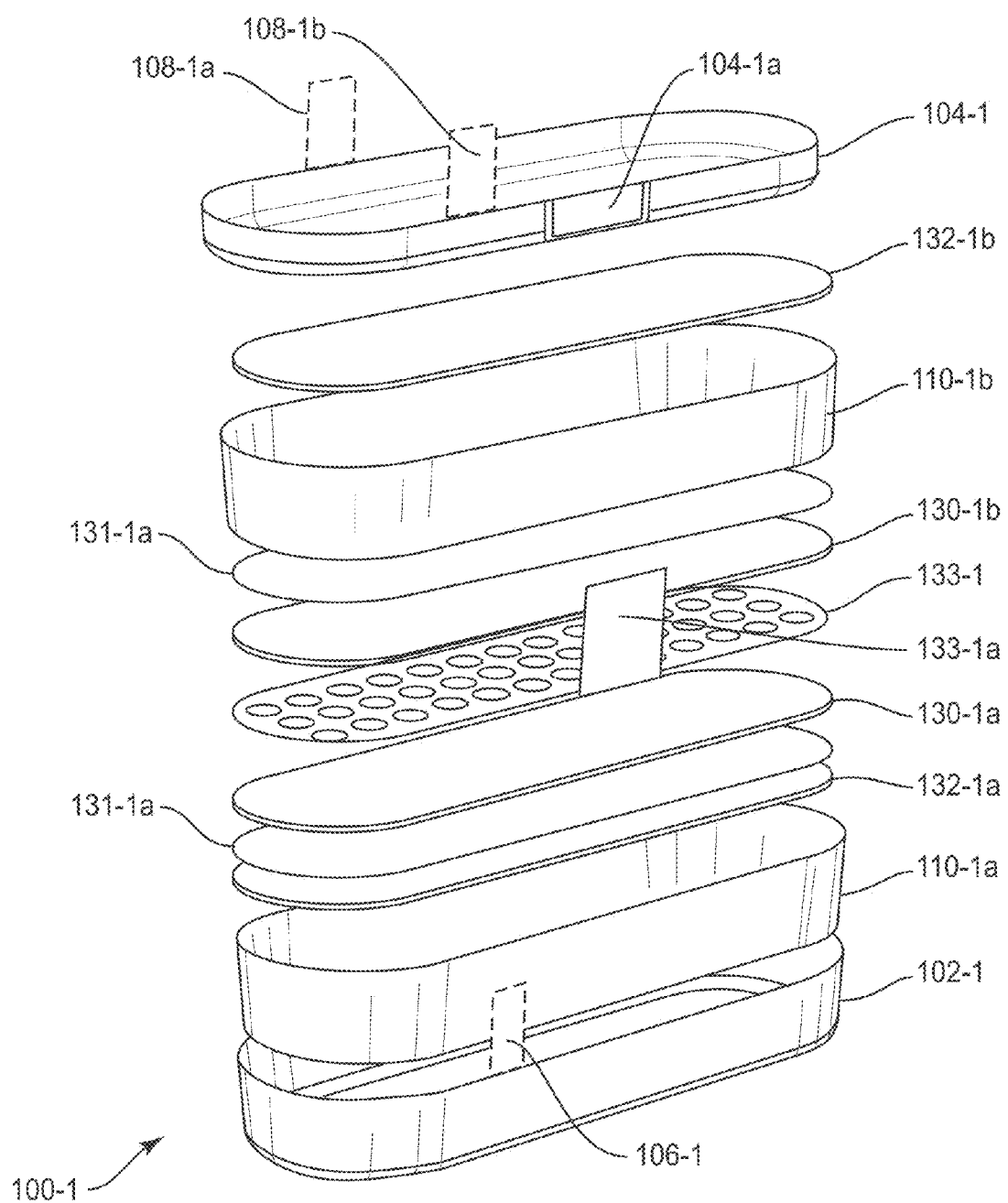
FIG. 1e is an exploded perspective view of a variation of the first embodiment of a battery housing shown in FIGS. 1a-1d wherein an intermediary current collector is disposed between electrode materials.

Referring to FIG. 1*e*, an alternative variation of the housing 100 is presented as alternative housing 100-1 which has first and second housing shells, 102-1 and 104-1, similar in configuration to corresponding housing shells of the housing 100. The alternative housing 100-1 and battery components thereof are formed of like materials as corresponding components of the housing 100 and battery components thereof. In contrast to the embodiment of FIG. 1*d*, the alternative housing 100-1 is configured to include a first set of a cathode electrode, separator, and anode electrode, 130-1*a*, 131-1*a*, and 132-1*a*, and a second set of a cathode electrode, separator, and anode electrode, 130-1*b*, 131-1*b*, and 132-1*b*. In an embodiment the anode electrodes, 132-1*a* and 132-1*b*, are lithium metal and the sealing material is acid modified polypropylene as employed in the aforementioned housing 100.

Further differentiating the alternative housing 100-1 and battery components from the first housing 100 and its associated battery components is the inclusion of a current collector 133-1 having a collector contact tab 133-1*a*. The current collector is interposed between the cathode electrodes, 130-1*a* and 130-1*b*, and is formed of a conductive material which does not adversely interact with the cathode electrodes, 130-1*a* and 130-1*b*, for example and not limitation, titanium, nickel, or copper may be used. The current collector 133-1 is depicted as a perforated plate but may also be formed without perforations. Furthermore, the current collector 133-1 may take the form of a screen or mesh impregnated with the cathode material so that the cathode electrodes, 130-1*a* and 130-1*b*, and the current collector 133-1 are formed as a unit prior to assembly of the battery components and housing. Alternatively, the reverse of the aforementioned embodiment may be employed such that the anode is pressed onto the current collector 133-1 and the cathode is place on the case 102-1 and cover 104-1. A first sealing sleeve 110-1*a* serves to insulate the first housing shell 102-1 from the cathode electrode 130-1*a* and the current collector 133-1 and the contact tab 133-1*a*. A second sealing sleeve 110-1*a* serves to insulate the contact tab 133-1*a* from the anode electrode 132-1*b* and the second housing shell 104-1. Still further, the first and second sealing sleeves, 110-1*a* and 110-1*b*, seal the battery components inside the first and second housing shells, 102-1 and 104-1.

The second housing shell 104-1 optionally includes a tab easement 104-1a to provide clearance for the contact tab 133-1*a* to pass between the first and second sealing sleeves, 110-1*a* and 110-1*b*, and the first and second housing shells 102-1 and 104-1. Alternatively, an easement may be placed in the first housing shell 102-1. Still further, an easement may be omitted and deformation and compression of the first and second sealing sleeves, 110-1*a* and 110-1*b*, may simultaneously provide for passage of the contact tab 133-1*a* and sealing of the first and second housing shells 102-1 and 104-1.

The first anode electrode 132-1*a* makes contact with the first housing shell 102-1 and the second anode electrode 132-1*b* makes contact with the second housing shell 104-1, each of which serve as a battery terminal. The first housing shell 102-1 is optionally provided with a first shell contact tab 106-1 and the second housing shell 104-1 is optionally provided with a second shell contact tab 108-1*a* which, in conjunction with the collector contact tab 133-1*a*, serve to supply power to an electronics assembly (not shown). In such an arrangement, the battery components provide two battery cells with the current collector 133-1 serving as a common terminal while the first and second housing shells, 102-1 and 104-1, and their associated contact tabs, 106-1 and 108-1*a*, provide terminals of independent cells which may have their respective anode electrodes, 132-1*a* and 132-1*b*, configured to provide differing power capacities, or characteristics. Alternatively, the second housing shell 104-1 is optionally provided with a second shell alternative contact tab 108-1*b*, instead of the prior mentioned second shell contact tab 108-1*a*. The second shell alternative contact tab 108-1*b* is positioned to coincide with the first shell contact tab 106-1 so that when assembly is completed, the first shell contact tab 106-1 contacts the second shell alternative contact tab 108-1*b*, and the two battery cells are thereby connected in parallel to supply current to an electronics assembly (not shown).

It is to be understood, that the use of the contact tabs shown may include disposing the contact tabs at different positions than those shown and also may include multiple contact tabs for each terminal. Alternatively, contact tabs may be omitted and replaced with wiring, spring contacts, built-in circuitry or the first and second housing shells 102-1 and 104-1 and first and second sealing sleeves, 110-1*a* and 110-1*b*, may be variously notched to expose portions of the first and second housing shells, 102-1 and 104-1, to wiring or contacts of an electronics assembly so as to facilitate powering the electronics assembly. Other methods of applying power to the electronics assembly (not shown) may be adapted by those skilled in the art having the benefit of the present disclosure. Still further, while a lithium type battery is provided as an example, other types of battery chemistries may be employed.

Figure 2:
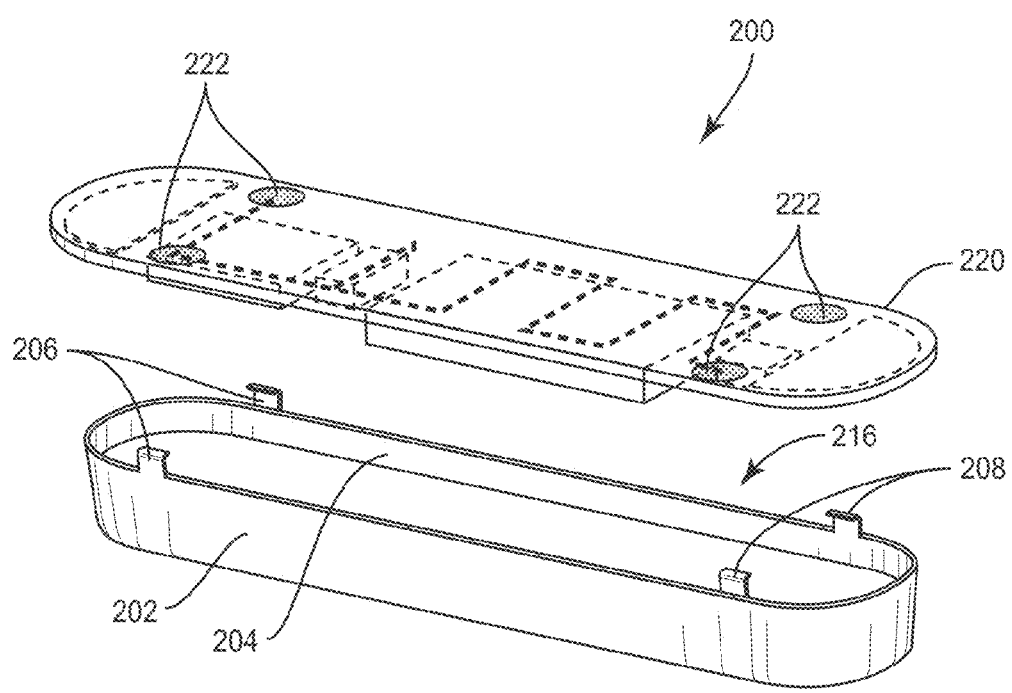
FIG. 2 is a front, top and right side perspective view of another embodiment of a battery housing of the present disclosure further showing a circuit board assembly in exploded relation to the embodiment of the battery housing.

Referring to FIG. 2, a second embodiment is shown comprising battery housing 200 which is of construction similar to the embodiment of FIGS. 1*a*-1*d* except as discussed herein. Elements corresponding to like elements of the first embodiment are given reference designators with 100 added. The second battery housing 200 has a first housing shell 202, and a second housing shell 204. An electronic assembly cavity 216 is defined in an upper portion of the battery housing 200 and configured to accept an electronic assembly 220 which is disposed in the electronic assembly cavity 216 followed by first and second conductor tabs, 206 and 208, being deformed to make contact with corresponding contact pads 222 which are optionally formed as bonding pads. Connections are optionally effected by mechanical pressure, soldering, conductive epoxy or other conductive adhesive material, or ultrasonic welding. Other forms of electrical interconnections such as clips, or wire/ribbon bonds are optionally employed. The electronic assembly 220 is thereby powered by the battery components via the first and second conductor tabs, 206 and 208, and the contact pads 222. In some embodiments, a medical device includes battery housing 200, as described herein, and the medical device may be surgically implanted in or carried on a patient.

Figure 3A:
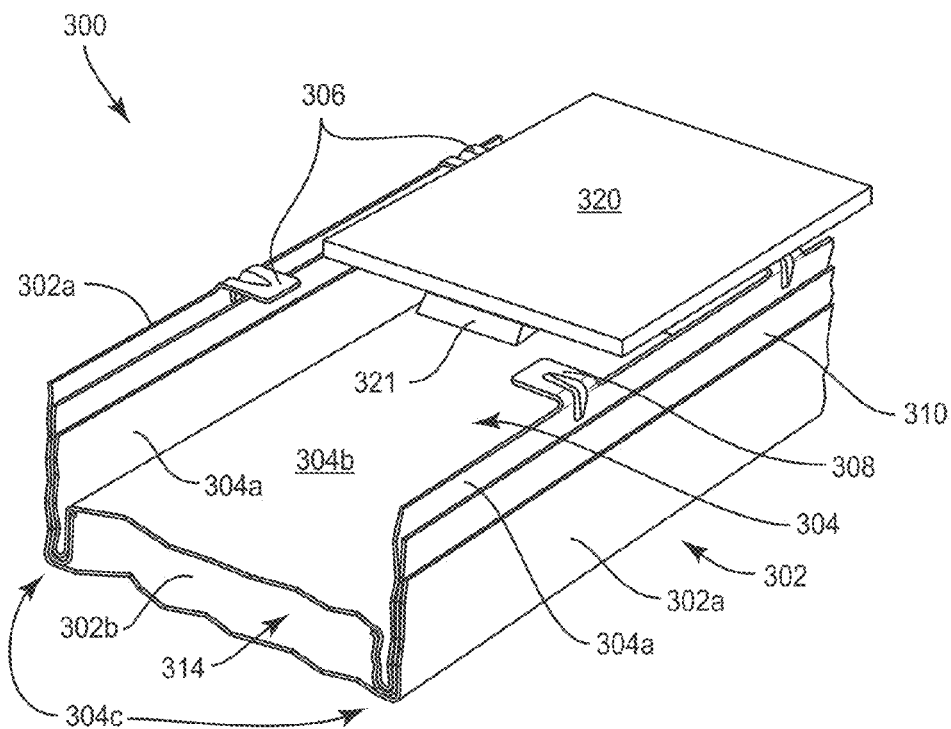
FIG. 3a is a front, top, and left side partial perspective cross-sectional view of another embodiment of a battery housing of the present disclosure.
Figure 3B:
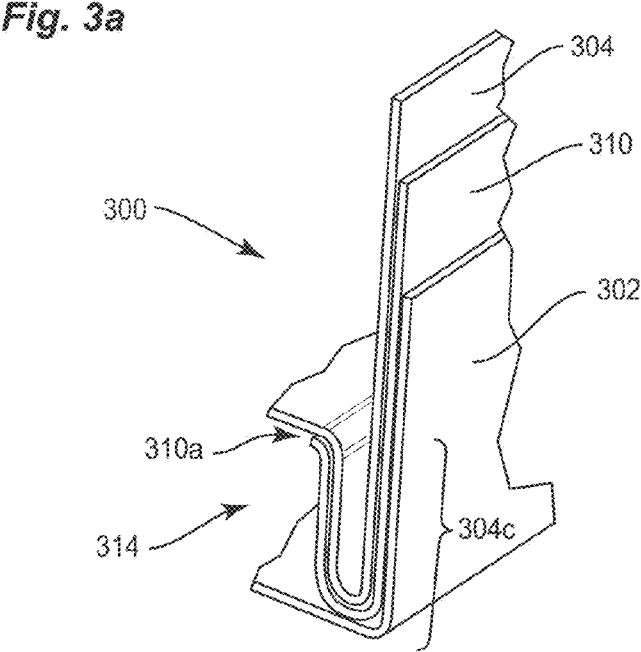
FIG. 3b is a front, top, and left side partial perspective cross-sectional view of a magnified portion of the embodiment of a battery housing of FIG. 3b.

In place of the insulating sealing member 110 of the first embodiment, which may be either molded or thermoformed, an insulating film (not shown) separates the first and second housing shells 202 and 204, as illustrated in a further embodiment of FIGS. 3*a* and 3*b*. The battery housing 200 is drafted, ensuring proper loading of a seal joint effected by the insulating film. Again, the insulating sealing member may be formed of the above noted PPaF or other insulating material.

The electronic assembly 220 is configured to nest in the second battery housing 200. In the second embodiment, as shown, the electronic assembly 220 nests in the second housing shell 204. Alternatively, the second housing shell 204 is optionally configured not to extend to an upper edge of the first housing shell 202 and the electronic assembly 220 nests within the first housing shell 202. In an embodiment, the nesting constitutes a press fit and heat is applied to reflow the insulating film to effect a seal. Alternatively, a press fit is not required and a sealing compound may be used to effect a seal between the electronic assembly 220 and the second battery housing 200. In one embodiment, the electronic assembly 220 is a printed circuit board having an antenna formed therein for purposes of any of communication, control, or charging.

Referring to FIGS. 3*a* and 3*b*, a third embodiment of a battery housing 300 has construction similar to the embodiments of FIGS. 1*a*-1*d*, and FIG. 2, except as discussed herein. Elements corresponding to like elements of the first embodiment or second embodiment are given reference designators with 200 or 100 respectively added. Although not shown, it is to be understood that the battery housing 300 is closed at ends not shown in a manner similar to that of the battery housings 100 and 200 shown in FIGS. 1*a*-1*d* and 2, to form a sealed battery components cavity 314. Additionally, it will be understood that battery components are omitted for clarity purposes in FIGS. 3*a*-3*b* but that, in completed form, the battery housing 300 will enclose battery components such as the anode electrode 132, cathode electrode 130 and separator 131 shown in FIG. 1*d*. In some embodiments, a medical device includes battery housing 300, as described herein, and the medical device may be surgically implanted in or carried on a patient.

The battery housing 300 has electrical contact tabs, 306 and 308, disposed to attach to bonding pads on an electronic assembly 320 having electronic components 321. It will be understood in light of this disclosure that electrical interconnect tabs can be distributed as required by applications. A first housing shell 302 is formed by drawing. A second housing shell 304 is formed by bonding an insulating film 310, such as for example a PPaF film, to a planar conductive sheet, titanium foil for example. In the third embodiment 300, an acid modified PP is used. The bonded assembly is then formed by drawing and folding the sheet to form the second housing shell 304. A contact aperture 310*a* is formed in the insulating film 310 to expose a contact area corresponding to the second contact area 113*b* of the first embodiment.

The first and second housing shells, 302 and 304, are formed into cup configurations respectively, having a first and second perimeter side wall, 302*a* and 304*a*, defining at top edges (based on normal cup orientations—opening at top) housing apertures, and first and second housing bottoms 302*b* and 304*b*. Although not depicted in FIGS. 3*a* and 3*b*, the first and second housing shells, 302 and 304, have the first and second perimeter side walls, 302*a* and 302*b*, extending around perimeters of the first and second housing shells, 302 and 304, to define the cup configurations. The second housing shell 304 has a folded region 304*c*, exemplarily embodied as a U-fold, which serves to increase sealing contact area between the insulating film 310 and the first housing shell 302 in comparison with the embodiment of FIGS. 1*a*-1*d*, while defining a height of a battery components cavity 314 by virtue of a bottom edge of the folded region 304*c* contacting an interior bottom of the first housing shell 302. The term "U-fold" as used herein is intended to mean a configuration wherein material is folded back on itself to form a U shape, and to include opposing facing sides of the material being either spaced apart or in contact with one another. The folded region 304*c* also provides added rigidity to the battery housing 300. Furthermore, the folded region 304*c* has the insulating film 310 extending up a side of the battery components cavity 314 which prevents shorting of battery components which are stacked, at least in part, in the vertical direction of FIGS. 3*a* and 3*b*, since edges of layers of the battery components will contact the insulating film 310 and will comprise at least one of both a cathode and an anode of the battery components.

The insulating film 310, in the illustrated embodiment, is applied to the second housing shell 304 as film layered on and bonded to the second housing shell 304. Alternatively, the insulating film 310 may take the form of a coating painted on the second housing shell 304, or a molded, thermoformed or cast, or machined configuration interposed between the first and second housing shells, 302 and 304. The insulating film 310 may be applied prior or subsequent to the drawing and forming.

Figure 4:
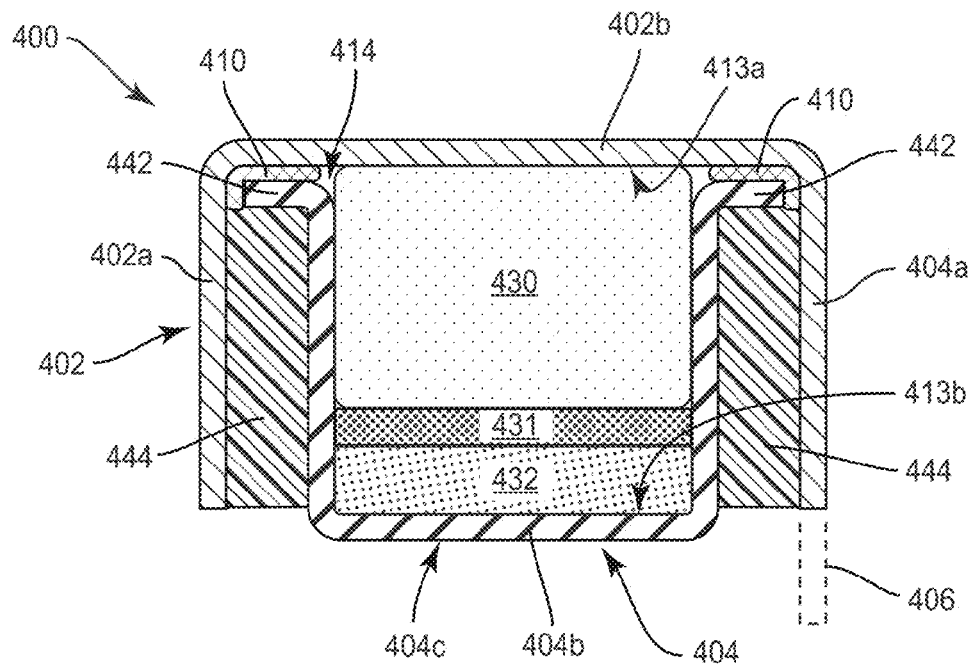
FIG. 4 is a front cross-sectional view of yet another embodiment of the battery housing of the present disclosure.

Referring to FIG. 4, a fourth embodiment of a battery housing 400 has a construction similar to the embodiments of FIGS. 1*a*-1*d*, 2, 3*a* and 3*b* except as discussed herein. Elements corresponding to like elements of the first embodiment, second or third embodiment are given reference designators with 300, 200 or 100 respectively added. The battery housing 400 has first and second housing shells 402 and 403. The first and second housing shells, 402 and 404, are formed into cup configurations respectively having a first and second perimeter side wall, 402a and 404a, defining at top edges housing apertures, and first and second housing bottoms 402b and 404b (based on normal cup orientations—opening at top—wherein the first housing shell 402 is inverted from the depicted orientation). Although not depicted in FIG. 4, the first and second housing shells, 402 and 404, have the first and second perimeter side walls, 402a and 402b, extending around perimeters of the first and second housing shells, 402 and 404, to define the cup configurations. The second housing shell 404 is formed to have a sealing flange 442 which, in conjunction with an insulating film 410 and sealing compound 444, seals a battery components cavity 414. The sealing compound may be any commonly used room temperature vulcanizing rubber compound, or similar silicone, or other polymer or natural type compounds used for sealing and potting. In some embodiments, a medical device includes battery housing 400, as described herein, and the medical device may be surgically implanted in or carried on a patient.

The battery housing 400 optionally has one or more electrical contact tabs 406 extending from a bottom edge (as oriented in FIG. 4) of the first housing shell for effecting battery terminals contacting an electronic assembly (not shown). A bottom contact surface 404c of the second housing shell 404 serves as another terminal of the battery housing 400. Opposing sides of the first housing shell 402 are optionally extended downward in FIG. 4 to further define an electronic assembly cavity similar to that of the first, second and third battery housings 100, 200 and 300.

An anode electrode, separator, and cathode electrode, 432, 431, and 430, comprise battery components installed in the battery components cavity 414. The separator 431 is optionally formed of a polymer electrolyte membrane (PEM). The insulating film is optionally extended down the interior wall of the second housing shell 404 to prevent shorting of the anode and cathode electrode, 432 and 430, or the anode electrode 432, separator 431, and cathode electrode 430 are assembled with an insulator surrounding vertical sides (as shown in FIG. 4) of the components, 430-432, to prevent shorting when the components are installed in the battery components cavity 414. As in the prior embodiments, the first and second housing shells, 402 and 404, have exposed areas serving as first and second contact areas 413a and 413b for electrically contacting the cathode electrode 430 and anode electrode 432 respectively as shown or vice versa depending on a desired polarity of the battery housing 400. The first housing shell 402 is optionally configured to have one or more electrical contact tabs 406 which can be used to connect to an electronic assembly.

Figure 5:
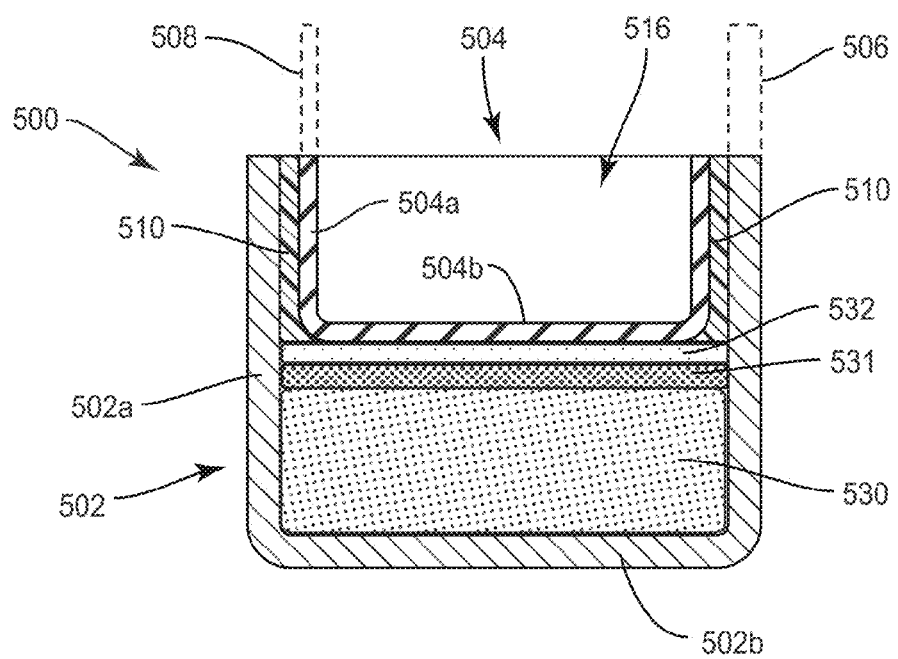
FIG. 5 is a front a cross-sectional view of still another embodiment of the battery housing of the present disclosure.

Referring to FIG. 5, a fifth embodiment of a battery housing 500 has a construction similar to the embodiments of FIGS. 1a-1d, 2, 3a, 3b and 4, except as discussed herein. Elements corresponding to like elements of the first embodiment, second or third embodiment are given reference designators with 400, 300, 200 or 100 respectively added. The battery housing 500 has first and second housing shells 502 and 504. The first and second housing shells, 502 and 504, are formed into cup configurations respectively having a first and second perimeter side wall, 502a and 504a, defining at top edges (based on orientations depicted) housing apertures, and first and second housing bottoms 502b and 504b. Although not depicted in FIG. 4, the first and second housing shells, 502 and 504, have the first and second perimeter side walls, 502a and 502b, extending around perimeters of the first and second housing shells, 502 and 504, to define the cup configurations. In some embodiments, a medical device includes battery housing 500, as described herein, and the medical device may be surgically implanted in or carried on a patient.

Optionally, extending from the first and second housing shells, 502 and 504, are electrical contact tabs, 506 and 508, for applying power to an electronic assembly. An insulating film 510 is carried on the second housing shell 504. A cathode electrode 530 and an anode electrode 532 are space apart by a separator 531 optionally formed of a polymer electrolyte membrane (PEM). Other types of separators may be employed along with added electrolytes to effect a functional battery cell. The anode electrode 532 is optionally formed of lithium and the cathode electrode 530 is formed of any of several complementary compounds to produce a lithium ion cell for example. The separator 531 is optionally staked in position between the insulating film 510 and the first housing shell 502. Alternatively, the insulating film 510 may be disposed on the first housing shell 502 and the separator 531 staked between the insulating film 510 and the second housing shell 504. It is appreciated that the present disclosure is not limited to this type of battery cell and that other known and yet to be known combinations of battery component materials may be adapted to any of the embodiments of battery housings described herein.

Referring to FIGS. 6a-6d, a sixth embodiment of a battery housing 600 has been fabricated using titanium foil of 75 μm and 50 μm thickness. Lithium ion battery components employing a lithium compound anode 632, a polymer electrolyte membrane separator 631, and a complementary cathode 630 were installed in the battery housing 600 during construction. The lithium ion battery components form a solid state battery by virtue of the use of the polymer electrolyte membrane separator 631. In the exemplary embodiment shown, the dimensions of the fabricated battery housing 600 are approximately 1.5 cm×0.5 cm and 1.5 mm thickness. In some embodiments, batteries are constructed and electrically tested. The capacity of the fabricated battery is approximately 48 mAhr. Battery housings of other dimensions and battery components are considered within the scope of the present disclosure.

Figure 6A:
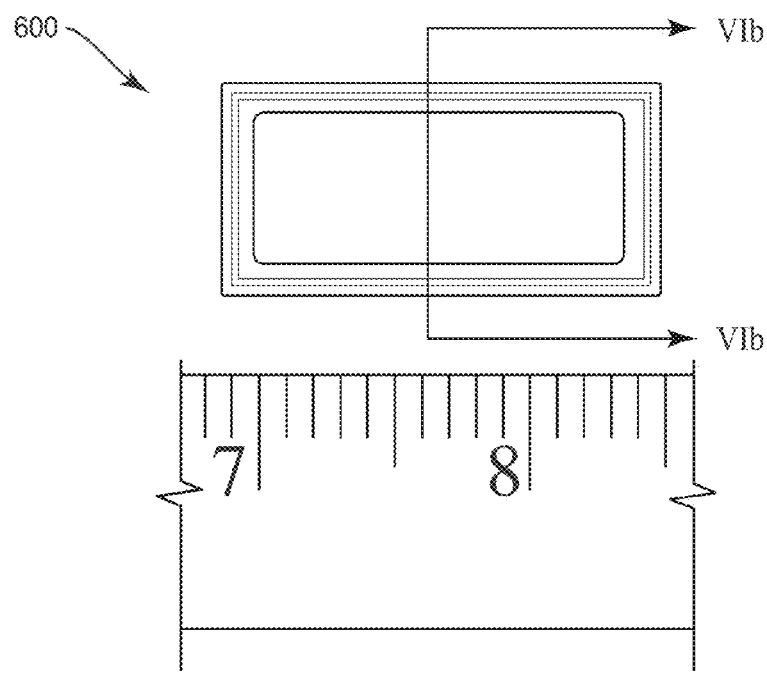
FIG. 6a is a top plan scale view of still another embodiment of the battery housing of the present disclosure showing a scale to indicate a size of the battery housing.
Figure 6B:
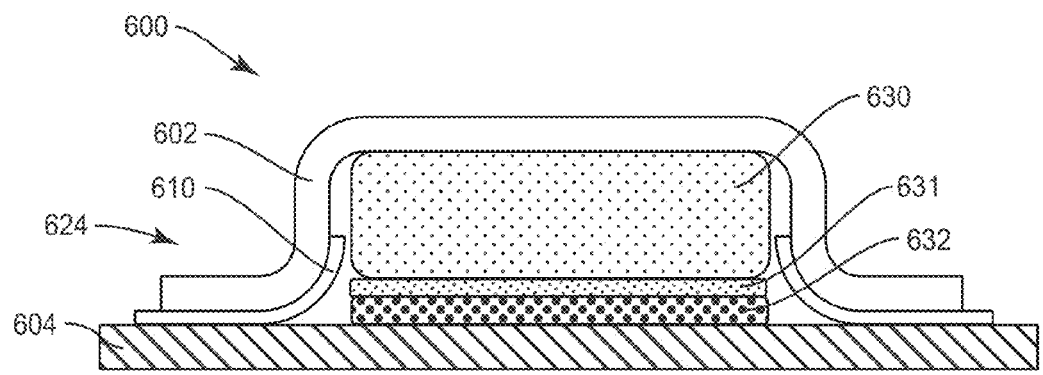
Figure 6C:
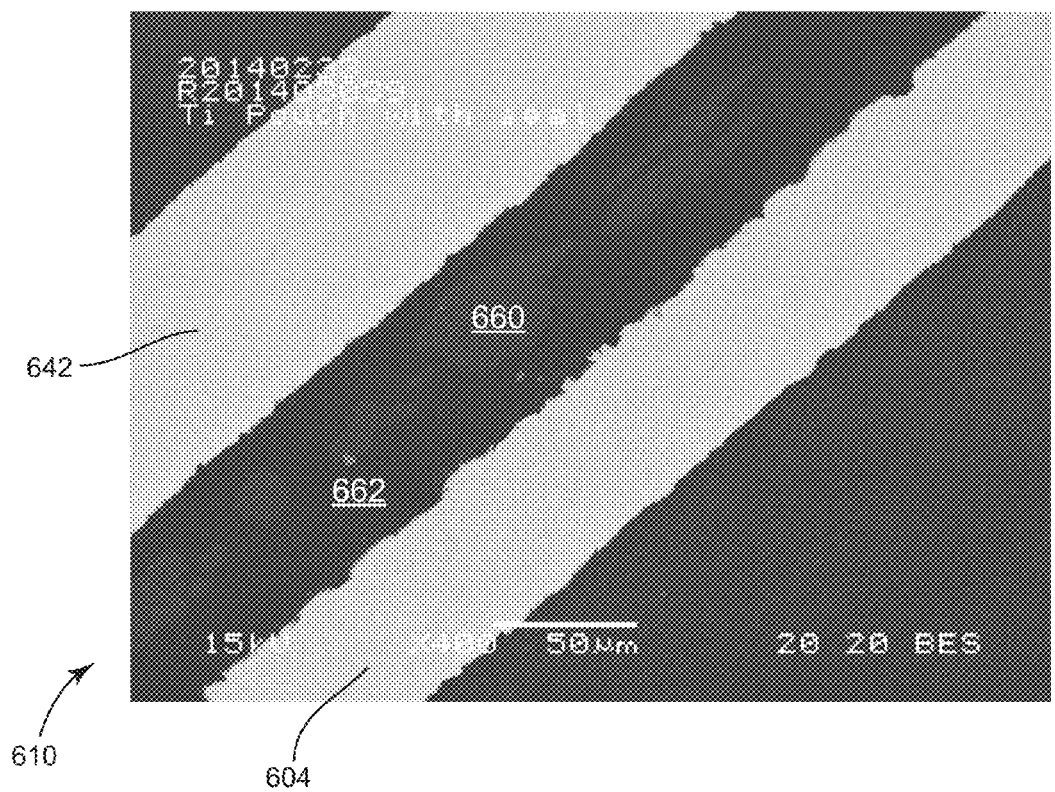
FIG. 6c is an electron microscope photograph of a cross section of a seal of first and second housing shells of the battery of FIG. 6a showing para-aramid synthetic fiber such Kevlar, Twaron, Nomex or Technora fibers in an acid modified polypropylene (PPaF) film seal material.

The battery housing 600 optionally includes a first housing shell 602 and a second housing shell 604 fabricated using the titanium foil of 75 μm and 50 μm thickness. An insulating sealing film 610, formed of, for example and not limitation, the aforementioned PPaF material, is used to seal and electrically isolate the first and second housing shells 602 and 604. Referring to FIG. 6c, the insulating sealing film 610 is sandwiched between a flange 642 of the first housing shell 602 and the second housing shell 604 and includes fibers 660 formed of Kevlar imbedded in the PPaF material 662 for the purpose of insuring isolation of the first and second housing shells, 602 and 604, when the first and second housing shells, 602 and 604, are pressed and bonded together by reflow of the PPaF material 662. As noted above, other materials may be embedded in the PP material to prevent punch through of the seal. In the battery housing 600, the insulating sealing film 610 acts to insulate the lithium compound anode 632 from the first housing shell 602 allowing the first housing shell 602 to act as a positive terminal while the second housing shell 604 acts as a negative terminal. It is to be understood that the polarity of the terminals may be reversed.

Figure 6D:
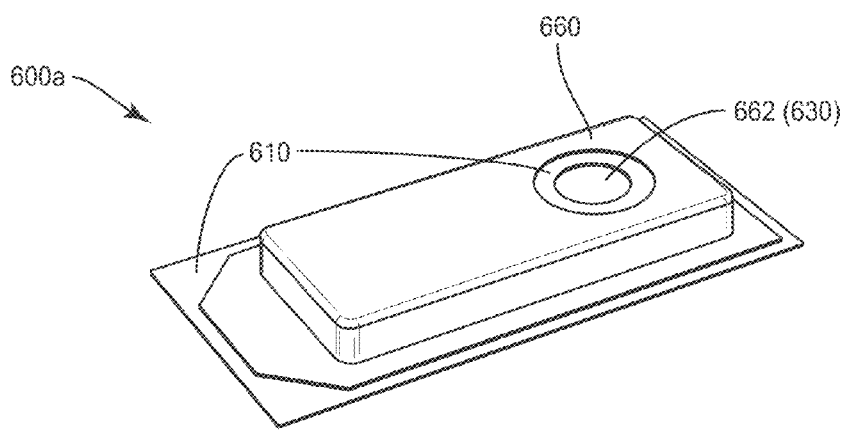
FIG. 6d is a perspective view of still another embodiment of the battery housing of the present disclosure showing an aperture in the first housing shell exposing a collector terminal.

An alternative configuration is shown in FIG. 6d wherein the insulating film 610 insulates the first housing shell 602 from the cathode 630, and an aperture 660 permits exposure of a collector 662 (or the cathode 630) to operate as a terminal. It will be understood by those skilled in the art having the benefit of the present disclosure that other terminal arrangements may be employed. For example and not limitation, two apertures exposing positive and negative collectors are used, or tabs formed of foil protruding through the apertures are used. Still further, the tabs may be formed of spring material to form biased contacts.

In the foregoing embodiments, the battery components are shown as comprising one battery cell. However, it is to be understood that the present disclosure also includes the use of multiple cells within the battery housings to provide varying voltage outputs. Furthermore, it is to be understood that the battery housings 100, 200, 300, 400, and 500, are not limited to the use of titanium foil and other formable conductive materials may be employed, such as, for example, and without limitation, aluminum, steel, copper, silver, gold and alloys thereof, or conductive non-metallic materials. Alternatively, non-conductive materials may be used incorporating conductive paths, i.e., conductor runs, in the form of any of applied conductive material such as foil, printed circuit, impregnated metal, or metal conductors (metallic or non-metallic) molded into either of the first and second housing shells, 102, 104, 202, 204, 302, 304, 402, 404, 502 and 504.

In the above embodiments, the first and second housing shells 102, 104, 202, 204, 302, 304, 402, 404, 502, 504, 602 and 604 are exemplary of monolithic construction being formed of sheet material in the form of titanium foil which is stamped and/or drawn and/or folded into the illustrated embodiments. However, the first and second housing shells 102, 104, 202, 204, 302, 304, 402, 404, 502, 504, 602 and 604, need not be of monolithic construction and may instead be formed of assembled portions. Still further, the first and second housing shells 102, 104, 202, 204, 302, 304, 402, 404, 502, 504, 602 and 604, need not be stamped, drawn or folded but may instead be molded, machined, deposited into a desired configuration. Likewise, use of titanium foil is exemplary and other materials and material configurations may be employed besides foil. Additionally, while the first and second housing shells 102, 104, 202, 204, 302, 304, 402, 404, 502, 504, 602 and 604, generally are combined to form an elongated tub configuration, it is within the scope of the present disclosure to form the first and second housing shells 102, 104, 202, 204, 302, 304, 402, 404, 502, 504, 602 and 604, in circular, square, or partially rounded and partially rectangular configuration as best suits a given application. Furthermore, the second housing shells 104, 204, 304, 404, 504 and 604, are optionally dimensioned to effect a press fit inside the first housing shells 102, 202, 302, 402, 502 and 602, when the insulating sealing member 110, the insulating film 210, 310, 410, 510 or the insulating sealing film 610, is respectively interposed therebetween. Alternatively, an insulating compound may be used which operates as an adhesive filling a space between the first housing shells 102, 202, 302, 402, 502 and 602, and the second housing shells 104, 204, 304, 404, 504 and 604. Still further, a press fit may be used in conjunction with an insulating surface treatment of at least one of the first and second housing shells 102, 104, 202, 204, 302, 304, 402, 404, 502, 504, 602 and 604, such anodization of various types which are dependent upon the material composition of the first and second housing shells 102, 104, 202, 204, 302, 304, 402, 404, 502, 504, 602 and 604.

Having described preferred embodiments of the disclosure with reference to the accompanying drawings, it is to be understood that the disclosure is not limited to those precise embodiments, and that various changes and modifications may be effected therein by one skilled in the art without departing from the scope or spirit of the disclosure as defined in the appended claims. Such modifications include substitution of components for components specifically identified herein, wherein the substitute components provide functional results which permit the overall functional operation of the present disclosure to be maintained. Such substitutions are intended to encompass presently known components and components yet to be developed which are accepted as replacements for components identified herein and which produce a result compatible with operation of the present disclosure. Furthermore, while examples have been provided illustrating operation at certain power levels, the present disclosure as defined in this disclosure and claims appended hereto is not considered limited to power levels recited herein.

What is claimed is:

1. A battery assembly comprising:
   a first housing shell having a first perimeter side wall, a first housing bottom, and a first contact area on said first housing bottom;
   a second housing shell having a second perimeter side wall, a second housing bottom, and a second contact area on said second housing bottom, said second housing shell being disposed in said first housing shell with said second contact area opposing said first contact area;
   an insulator interposed between said first housing shell and said second housing shell to effect electrical insulation between said first housing shell and said second housing shell; and battery components comprising:
      an anode electrode electrically communicated to one of said first contact area or said second contact area;
      a cathode electrode electrically communicated to another one of said first contact area or said second contact area; and
      a separator interposed between said cathode electrode and said anode electrode, said separator including an electrolyte,
   wherein said first housing bottom of said first housing shell opposes said second housing bottom of said second housing shell to define a battery component cavity in conjunction with said first perimeter side wall of said first housing shell, and said anode electrode, said separator, and said cathode electrode are disposed in said battery component cavity,
   wherein at least one of said first perimeter side wall or said second perimeter side wall in conjunction with said second housing bottom define an electronic assembly cavity, and
   wherein:
      said second perimeter side wall has a perimeter edge defining an opening aperture of said second housing shell and a perimeter flange extending outward from said perimeter edge in a direction away from an interior of said second housing shell;
      said second housing is disposed within said first housing shell such that said insulator is situated between said perimeter flange and said first housing bottom, and said first housing shell has a cup configuration inverted from a cup configuration orientation of said second housing shell; and said first perimeter side wall, said second perimeter side wall, and said perimeter flange define, at least in part, an inter-shell cavity between said first housing shell and said second housing shell; and a sealing compound disposed in said inter-shell cavity.

2. A battery assembly according to claim 1, wherein said first housing shell includes at least one first contact projecting from said first perimeter side wall.

3. A battery assembly according to claim 2, wherein said second housing shell includes at least one second contact projecting from said second perimeter side wall.

4. A battery assembly according to claim 3, further comprising an electronic assembly disposed in said electronic assembly cavity, and said at least one first contact and said at least one second contact electrically contacting said electronic assembly to provide power from said battery components.

5. A battery assembly according to claim 4, wherein said insulator is an insulating film laminated on at least one of said first housing shell and said second housing shell.

6. A battery assembly according to claim 5, wherein said insulator includes at least one of fibers, alumina particles, or glass spheres configured to effect separation and electrical isolation of said first housing shell and said second housing shell.

7. A battery assembly according to claim 3, wherein said insulator is a molded insulator configured to form a sleeve between said first and second housing shells.

8. A battery assembly according to claim 3, wherein said second perimeter side wall includes a U-fold extending from said second housing bottom toward said first housing bottom and defines at least a portion of said battery components cavity.

9. A battery assembly according to claim 8, wherein said U-fold has first and second opposite outer surfaces and said insulator is disposed on said first and second opposite outer surfaces.

10. A battery assembly according to claim 1, further comprising an electronic assembly disposed in said electronic assembly cavity, and said electronic assembly being electrically connected to said first and second housing shells to provide power from said battery components, wherein said insulator is an insulating film laminated on at least one of said first housing shell and said second housing shell.

11. A battery assembly according to claim 1, further comprising an electronic assembly disposed in said electronic assembly cavity, and said electronic assembly being electrically connected to said first and second housing shells to provide power from said battery components, wherein said insulator includes at least one of fibers, alumina particles, or glass spheres configured to effect separation and electrical isolation of said first housing shell and said second housing shell.

12. A battery assembly according to claim 11, wherein said insulator is a molded insulator configured to form a sleeve between said first and second housing shells.

13. A battery assembly according to claim 1, further comprising an electronic assembly disposed in said electronic assembly cavity, and said electronic assembly being electrically connected to said first and second housing shells to provide power from said battery components, wherein said second perimeter side wall includes a U-fold extending from said second housing bottom toward said first housing bottom and defines at least a portion of said battery components cavity.

14. A battery assembly according to claim 13, wherein said U-fold has first and second opposite outer surfaces and said insulator is disposed on said first and second opposite outer surfaces.

15. A battery assembly comprising:
a first housing shell having a first perimeter side wall, a first housing bottom, and a first contact area on said first housing bottom;
a second housing shell having a second perimeter side wall, a second housing bottom, and a second contact area on said second housing bottom, said second housing shell being disposed in said first housing shell with said second contact area opposing said first contact area;
an insulator interposed between said first housing shell and said second housing shell to effect electrical insulation between said first housing shell and said second housing shell;
battery components comprising:
an anode electrode electrically communicated to one of said first contact area or said second contact area;
a cathode electrode electrically communicated to another one of said first contact area or said second contact area; and
a separator interposed between said cathode electrode and said anode electrode, said separator including an electrolyte; and
an electronic assembly disposed in said electronic assembly cavity, and said electronic assembly being electrically connected to said first and second housing shells to provide power from said battery components, wherein said second perimeter side wall includes a U-fold extending from said second housing bottom toward said first housing bottom and defines at least a portion of said battery components cavity,
wherein said first housing bottom of said first housing shell opposes said second housing bottom of said second housing shell to define a battery component cavity in conjunction with said first perimeter side wall of said first housing shell, and said anode electrode, said separator, and said cathode electrode are disposed in said battery component cavity,
wherein at least one of said first perimeter side wall or said second perimeter side wall in conjunction with said second housing bottom define an electronic assembly cavity, and
wherein said U-fold has first and second opposite outer surfaces and said insulator is disposed on said first and second opposite outer surfaces.

16. A battery assembly according to claim 15, wherein said first housing shell includes at least one first contact projecting from said first perimeter side wall.

17. A battery assembly according to claim 16, wherein said second housing shell includes at least one second contact projecting from said second perimeter side wall.

18. A battery assembly comprising:
a first housing shell having a first perimeter side wall, a first housing bottom, and a first contact area on said first housing bottom;
a second housing shell having a second perimeter side wall, a second housing bottom, and a second contact area on said second housing bottom, said second housing shell being disposed in said first housing shell with said second contact area opposing said first contact area;
an insulator interposed between said first housing shell and said second housing shell to effect electrical insulation between said first housing shell and said second housing shell; and battery components comprising:
an anode electrode electrically communicated to one of said first contact area or said second contact area;
a cathode electrode electrically communicated to another one of said first contact area or said second contact area; and
a separator interposed between said cathode electrode and said anode electrode, said separator including an electrolyte,
wherein said first housing bottom of said first housing shell opposes said second housing bottom of said second housing shell to define a battery component cavity in conjunction with said first perimeter side wall of said first housing shell, and said anode electrode, said separator, and said cathode electrode are disposed in said battery component cavity,
wherein at least one of said first perimeter side wall or said second perimeter side wall in conjunction with said second housing bottom define an electronic assembly cavity,
wherein said first housing shell includes at least one first contact projecting from said first perimeter side wall,
wherein said second housing shell includes at least one second contact projecting from said second perimeter side wall,
wherein said second perimeter side wall includes a U-fold extending from said second housing bottom toward said first housing bottom and defines at least a portion of said battery components cavity, and
wherein said U-fold has first and second opposite outer surfaces and said insulator is disposed on said first and second opposite outer surfaces.

* * * * *